United States Patent [19]

Hay

[11] 4,254,252

[45] Mar. 3, 1981

[54] CYCLIC POLYFORMALS AND METHOD FOR MAKING

[75] Inventor: Allan S. Hay, Schenectady, N.Y.

[73] Assignee: General Electric Company, Schenectady, N.Y.

[21] Appl. No.: 905,637

[22] Filed: May 15, 1978

Related U.S. Application Data

[63] Continuation-in-part of Ser. No. 739,562, Nov. 8, 1976, abandoned.

[51] Int. Cl.$^3$ ............................................. C08G 65/40
[52] U.S. Cl. ................................... 528/205; 260/338; 528/219
[58] Field of Search ................... 260/47 R, 61, 613 R, 260/338; 528/205, 219

[56] References Cited

U.S. PATENT DOCUMENTS

| Re. 29,616 | 4/1978 | Takekoshi ........................... 260/17.2 |
| Re. 29,617 | 4/1978 | Takekoshi et al. ................. 260/17.2 |
| 3,069,386 | 12/1962 | Barclay, Jr. ............................. 260/49 |
| 3,534,064 | 10/1970 | Dietrich et al. ...................... 260/338 |
| 4,136,087 | 1/1979 | Williams et al. ..................... 528/219 |

*Primary Examiner*—Lester L. Lee
*Attorney, Agent, or Firm*—William A. Teoli; James C. Davis, Jr.

[57] ABSTRACT

Cyclic polyformals of 2,2'-bis(4-hydroxyphenyl)-1,1-dichloroethylene are provided and method for making such materials. The cyclic polyformals are useful as flame retardants, plasticizers and for making wire coated formulations in a variety of organic polymers, such as polycarbonates, polyesters, etc.

2 Claims, No Drawings

CYCLIC POLYFORMALS AND METHOD FOR MAKING

CROSS REFERENCES TO RELATED APPLICATIONS

This application is a continuation-in-part of my copending application Film Forming Moldable Aromatic Polyformal Resins and Method for Making Same, Ser. No. 739,562, filed Nov. 8, 1976 and now abandoned. This application is also related to my copending application Method for Making Polyformals and Polyformal Products Made Thereby, Ser. No. 889,393, filed Mar. 23, 1978 and now abandoned. In addition, this application is related to copending applications of George R. Loucks and Frank J. Williams, III, for Method for Making Aromatic Polyformals, Ser. No. 889,397, filed Mar. 23, 1978; copending application Ser. No. 905,635, filed May 15, 1978 and now U.S. Pat. No. 4,163,833 of Donald S. Johnson, for Method of Making Aromatic Cyclic Polyformals, filed concurrently herewith, and copending application Ser. No. 905,636, filed May 15, 1978 and now U.S. Pat. No. 4,136,087 of Frank J. Williams et al, for Method for Making Aromatic Cyclic Polyformals, where all of the aforementioned applications are assigned to the same assignee as the present invention.

BACKGROUND OF THE INVENTION

As shown in my copending application Ser. No. 889,393, film forming aromatic polyformals can be made having up to about 50% by weight of cyclic polyformals of the formula,

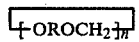 (1)

where R is a divalent aromatic organic radical, and n is an integer equal to from 2–25 inclusive, by agitating a mixture of methylene halide, bisphenol, alkali metal hydroxide with either a phase transfer catalyst or a dipolar aprotic solvent.

The cyclic polyformals of formula (1) have been found to be useful for making wire coating formulations when employed in combination with a Lewis Acid catalyst and an organic solvent.

The present invention is based on the discovery that aromatic cyclic polyformals of the formula,

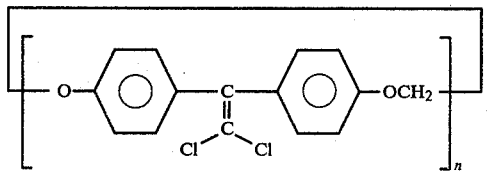 (2)

where n is an integer equal to 2–25 inclusive, can be made by my aforedescribed method utilizing 1,1-dichloro-2,2-(4-hydroxyphenyl)ethylene or "dichloride" as the bisphenol. The aromatic cyclic polyformals of formula (2) also can be used to make wire coated formulations when employed as an organic solvent solution with a Lewis Acid catalyst, such as $FeCl_3$, $H_2SO_4$, etc.

Another procedure which can be used to make aromatic cyclic polyformals of formula (2) is shown in the above described copending application Ser. No. 905,635, of Donald S. Johnson. In accordance with the procedure of Ser. No. 905,635, a bisphenol dianion is utilized in an aqueous phase at up to about 3% by weight in combination with excess alkali metal hydroxide, which in employed in further combination with a phase transfer catalyst and an organic phase comprising methylene chloride. The aqueous phase and the organic phase are maintained at about equal parts by volume while the mixture is agitated.

In addition to making wire coating formulations, the aromatic cyclic polyformals of formula (2) also can be blended with various organic polymers, such as polycarbonates, polyesters, etc., at proportions of from 1% to 25% by weight, resulting in thermoplastic materials having improved flame retardant properties.

In order that those skilled in the art will be better able to practice the invention, the following examples are given by way of illustration and not by way of limitation. All parts are by weight.

EXAMPLE 1

There was added 7.8 parts of sodium hydroxide pellets at 90% of theoretical weight to a stirred mixture of 30 parts of 1,1-dichloro-2,2-(4-hydroxyphenyl)ethylene, 78 parts of methylene chloride and about 80 parts of N-methyl-2-pyrrolidone. During the addition, the mixture was maintained at about 80° C. The mixture was refluxed for about 90 minutes and an additional 1.3 part of sodium hydroxide pellets and 0.45 part of p-tertbutyl phenol as a 5% solution in methylene chloride was added to the mixture. The mixture was stirred and refluxed for an additional 5 hours.

The mixture was allowed to cool to room temperature and diluted with about 450 parts of monochlorobenzene and filtered to remove sodium chloride. The clear polymer solution was then agitated vigorously while about 450 parts of a methanol-acetone blend containing 1% of acetic acid by volume was gradually added. The precipitate was collected by filtration and reslurried in methanol. The product was found to contain 12% to 15% by weight of cyclic polyformal of formula (2), based on gel permeation chromatography. The cyclic polyformal was isolated by high pressure liquid chromatography.

A saturated methylene chloride solution of the above cyclic polyformal is stirred with a diethylether-$BF_3$ complex to produce a 1% by weight complex solution. A copper wire is dipped into the solution and removed and allowed to air dry. A solvent resistant coating is found on the surface of the copper wire which has valuable insulating and flame retardant characteristics.

EXAMPLE 2

There was added to 4 parts of 1,1-dichloro-2,2-(4-hydroxyphenyl)ethylene, 100 parts of 50% sodium hydroxide pellets, 100 parts of water, 133 parts of methylene chloride, 2 parts of Aliquat 336, a phase transfer catalyst manufactured by the General Mills Company Chemical Division 85% active monomethyltricapryl ammonium chloride) and about 100 parts of chlorobenzene. The resulting mixture is stirred and refluxed for 23 hours. The reaction mixture is then allowed to cool to room temperature and it separates into 2 layers. The organic layer is recovered and dried over magnesium sulfate. Nitrogen is passed over the resulting organic solvent solution until the volume of the mixture is reduced to about ½ of its original volume. A significant amount of product separates from the mixture. Based on method of preparation, the product is an aromatic cyclic polyformal of the formula,

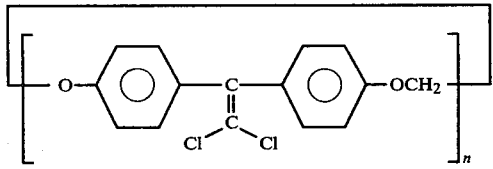

where n is an integer having a value of from 2–25 inclusive.

Although the above examples are directed to only a few of the very many variables which can be used in the practice of the present invention, it should be understood that the present invention is directed to additional uses of procedures for making the aromatic cyclic polyformals of formula (2) as shown in the description preceding these examples.

What I claim is new and desire to secure by Letters Patent of the United States is:

1. Cyclic polyformals of the formula,

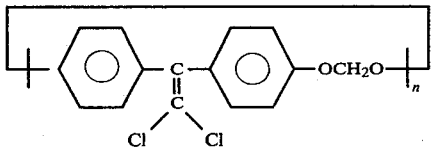

where n is an integer having a value of from 2–25 inclusive.

2. A cyclic polyformal of the formula,

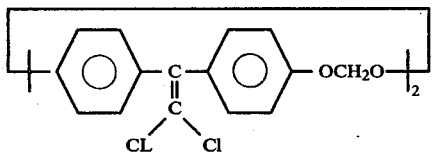

* * * * *